United States Patent [19]

Phillips et al.

[11] Patent Number: 5,710,332
[45] Date of Patent: Jan. 20, 1998

[54] CARBOHYDRATE-DERIVED SURFACTANTS AND THEIR PRECURSORS

[75] Inventors: Brynley Morris Phillips, Kidderminster; Ajit Kumar, West Bromwich; Alan Smithson, Kidderminster, all of England

[73] Assignee: Albright & Wilson Limited, Warley, England

[21] Appl. No.: 679,152

[22] Filed: Jul. 12, 1996

Related U.S. Application Data

[62] Division of Ser. No. 596,452, Feb. 2, 1996, abandoned, which is a division of Ser. No. 340,801, Nov. 16, 1994, Pat. No. 5,523,478, which is a continuation of Ser. No. 60,280, May 11, 1993, abandoned.

[30] Foreign Application Priority Data

| May 11, 1992 | [GB] | United Kingdom | 9210094 |
| May 11, 1992 | [GB] | United Kingdom | 9210133 |
| Mar. 3, 1993 | [GB] | United Kingdom | 9304273 |

[51] Int. Cl.$^6$ ............................................. C07C 291/00
[52] U.S. Cl. ............................................. 564/297; 564/298
[58] Field of Search ................................... 564/297, 298

[56] References Cited

U.S. PATENT DOCUMENTS

| 2,016,956 | 10/1935 | Calcott . |
| 2,016,962 | 10/1935 | Flint . |
| 2,016,963 | 10/1935 | Flint . |
| 2,060,851 | 11/1936 | Calcott . |
| 2,181,941 | 12/1939 | Goldacker . |

FOREIGN PATENT DOCUMENTS

| 0 396 871 | 11/1990 | European Pat. Off. . |
| 2 063 423 | 9/1972 | Germany . |
| 2 241 234 | 8/1991 | United Kingdom . |

OTHER PUBLICATIONS

Chemical Abstracts, vol. 82, No. 16, Apr. 21, 1975, p. 168, Abstract No. 100590d, Columbus, Ohion, US of Veksler et al & ZH. Obshck. Khim. vol. 44, No. 10, 1974, pp. 2367–2368.

*Primary Examiner*—Michael L. Shippen
*Attorney, Agent, or Firm*—Frishauf, Holtz, Goodman, Langer & Chick, P.C.

[57] ABSTRACT

A method for the manufacture of N,N dialkylglycamine compounds of general formula $R_2NR_1R_3$(I) by reacting a secondary amine of general formula $R_2NHR_3$(II) in which $R_2$ is a straight or branched chain alkyl or hydroxyalkyl group having from 1 to 4 carbon atoms and $R_3$ is a residue from a monosaccharide, with an alkali metal or alkaline earth metal aliphatic sulphate, $R_1SO_4M$, in which $R_1$ is a straight or branched chain alkyl or alkenyl group having from 8 to 24 carbon atoms.

The betaine, suphobetaine and N-oxidised derivatives of (I) are provided for use as mild surfactants.

3 Claims, No Drawings

CARBOHYDRATE-DERIVED SURFACTANTS AND THEIR PRECURSORS

This application is a Division, of application Ser. No. 08/596,452, filed Feb. 2, 1996, now abandoned, which is a division of application Ser. No. 08/340,801 filed Nov. 16, 1994, now U.S. Pat. No. 5,523,478, issued Jun. 4, 1996, which is a continuation application of Ser. No. 08/060,280 filed May 11, 1993, abandoned.

The present invention relates to an improved method for the production of carbohydrate derived surfactants and their precursors. More specifically it relates to an improved method for the production of N,N-dialkylglycamino compounds possessing at least one fatty alkyl chain, which are of value as intermediates in the manufacture of a variety of semipolar, amphoteric and cationic surfactants, and to certain novel derivatives thereof. The N-oxidised, N-carboxymethylated and N-sulphoalkylated derivatives of the aforesaid intermediates (amine oxides, betaines and sulphobetaines respectively) are novel compounds which are especially preferred according to the present invention.

Such novel compounds are particularly gentle on the skin and eyes and show low toxicity, being very effective as mild surfactants, especially in neutral or weakly acidic media. The compounds are derivatives of naturally-occurring and renewable raw materials such as carbohydrates and natural fats and oils, which is desirable on environmental and toxicological grounds. Surfactants which are derivatives of amines based on monosaccharides are particularly well tolerated physiologically.

EP 0 396 871 A2 discloses carboxymethylated derivatives of N-alkylglycamine. Dialkylated glycamines are described in the literature (Veksler et al, Zhur. Obshch. Khim., Vol.44, No. 10, pp 2328–2329) but a satisfactory way of producing them in a useful form has not been disclosed. The above literature reference describes a synthesis of N-alkyl-N-methyl-D-glucamine using an alkyl halide (a toxic, expensive reagent) as the alkylating agent. In the above synthesis cationic quaternary ammonium salts are also formed in the reaction. Such cationic species may be skin or eye irritants and therefore represent highly undesirable by-products with respect to amphoteric surfactant manufacture. For these reasons N,N-dialkylglycamino compounds have not been considered hitherto as suitable intermediates for amphoteric or semipolar surfactants such as are widely used in the cosmetics industry.

The present invention provides an improved method for the manufacture of N,N-dialkylglycamine compounds of general formula (I):

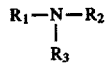

in which $R_1$ is a straight or branched chain alkyl or alkenyl group having from 8 to 24 carbon atoms, $R_2$ is a straight or branched chain alkyl or hydroxyalkyl group having from 1 to 4 carbon atoms and $R_3$ is a residue derived from a monosaccharide, which method comprises reacting a secondary amine of general formula (II):

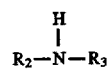

in which $R_2$ and $R_3$ are as hereinabove described, with an alkali metal or alkaline earth metal aliphatic sulphate $R_1SO_4M$, in alkaline solution, at a temperature sufficient to produce the N,N dialkylglycamine compound.

The proportions may be stoichiometric. An excess of either reagent is tolerable since both are water soluble and can be removed from the product by washing. The sulphate, being surface active, is less easily removed than the amine. Accordingly a small excess of amine is preferred.

Typically, in the method of the present invention, said secondary amine, eg. N-methyl-D-glucamine, and said sulphate, eg. sodium $C_{8-24}$ alkyl or alkenyl sulphate, especially sodium lauryl sulphate, are suitably charged to a reaction vessel, eg. an autoclave, in a molar ratio of from 5:1 to 1:1.5 (by weight amine: sulphate), especially from 4:1 to 1:1.1, more preferably from 3:1 to 1:1, eg 2:1 to 1.1:1 in the presence of a sufficient quantity of a suitable alkali, eg. an alkali metal or alkaline earth metal hydroxide, especially sodium hydroxide, to neutralise any acid formed, e.g. at a pH of at least 12.

The reaction vessel is preferably heated to a sufficient temperature such that an adequate reaction rate is maintained, whilst nevertheless avoiding excessive decomposition of the carbohydrate residue. Depending upon the type of reactor employed a suitable range may be from ambient temperature to 200° C. eg. 120° C. to 170° C., eg. 140° C. to 160° C., such as 150° C.

A typical reaction time is from 0.5 to 24 hours, eg. 1.5 to 10 hours, depending upon the temperature.

The product N,N-dialkylglycamine so obtained may be isolated by conventional means, such as washing with water and/or an organic solvent, eg. methanol. No additional purification stage is normally required.

The present invention further provides novel derivatives of N,N-dialkylglycamine compounds described by structure (I).

According to a preferred embodiment, the invention provides novel N,N-dialkylglycamine derivatives of general formula (III):

in which $R_1$, $R_2$ and $R_3$ are as hereinabove defined, and $R_4$ is a $CH_2CO$ or $CH_2CHOHCH_2SO_2$ group, and n is 1 or 0, ie. N,N-dialkylglycamino acetate, N,N-dialkylglycamino-2-hydroxy-3-sulphopropane or N,N-dialkylglycamine oxide respectively.

In the N,N-dialkylglycamine derivatives of formula (III), $R_1$ preferably has from 8 to 24 carbon atoms, e.g. 10 to 22, especially 12 to 14, being typically a fatty alkyl or alkenyl residue such as is derived from, e.g. oleic, linoleic, myristic, stearic, tauric, lauric or dodecanoic acid, $R_2$ is an alkyl or hydroxyalkyl group preferably having from 1 to 4 carbon atoms and is typically methyl, and $R_3$ may suitably be derived from hexose sugars such as D-glucose, D-galactose, D-mannose and D-fructose, thereby representing a deoxyhexityl group, such as

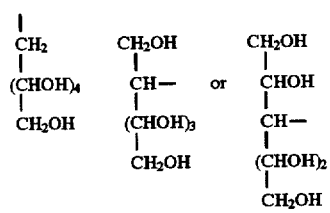

eg. 1-deoxy-1-glucityl, 2-deoxy-2-glucityl and 3-deoxy-3-glucityl, especially 1-deoxy-1-glucityl, most especially 1-deoxy-1-D-glucityl.

Typical examples of novel derivatives of N,N-dialkylglycamine compounds of formula (III) according to the present invention are N-dodecyl-N-methyl-D-glucamino acetate and N-dodecyl-N-methyl-D-glucamine N-oxide, and N-dodecyl-N-methyl-D-glucamino-2-hydroxy-3-sulphopropane.

The present invention further provides a method for the production of compounds of formula (III) derived from compounds of formula (I) made according to the method of the present invention, said method comprising:

(a) N-carboxymethylating N,N-dialkylglycamine (I) to produce N,N-dialkylglycamine acetate (b) contacting N,N-dialkylglycamine (I) with 3-chloro-2-hydroxypropane sulphonic acid or its salts to form the corresponding hydroxypropane sulphonate or (c) contacting N,N-dialkylglycamine (I) with an oxidising agent so as to form the corresponding N-oxide.

In steps (a) and (b) of the method of the present invention, to produce the N,N-dialkylglycamine acetate, or hydroxy propane sulphonate said N,N-dialkylglycamine, eg. N-dodecyl-N-methyl-D-glucamine is typically reacted with a suitable N-carboxymethylating agent or N-sulphoalkylating agent respectively using the same conditions as are conventionally used in the art for carboxymethylating or sulphoalkylating amine surfactants or surfactant precursors.

Suitable reagents include 3-chloro-2-hydroxypropane sulphonic acid, for sulphoalkylation and alkali metal chloroacetate, and especially sodium chloroacetate for carboxymethylation. Carboxymethylation is usually carried out in aqueous solution, although organic or other inert solvents can be employed as described in the prior art.

In a most preferred embodiment of step (a) of the method of the present invention, sufficient sodium chloroacetate is added to ensure substantially complete carboxymethylation of said N,N-dialkylglycamine, for example using a molar ratio of from 0.9:1 to 1.5:1 preferably stoichiometric ratios (sodium chloroacetate:glycamine) or a small excess of chloroacetate. A temperature and a pH such that the hydroxyl group of the monosaccharide residue, eg. deoxyhexityl group, does not react, and chloroacetate does not excessively hydrolyse to glycollate, are then maintained, with stirring, for from 1 to 30 hours, eg. 15 hours, dependent upon temperature. Typically the temperature may be maintained between ambient and the temperature at which degradation of the monosaccharide residue or the chloroacetate occurs e.g. up to 100° C., preferably 40°–90° C., such as 70° C., and the pH may for example be above 7, such as 8 to 9. Excess chloracetate can be hydrolysed to glycollate by heating the product under alkaline conditions.

The product N,N-dialkylglycamine acetate, eg. N-dodecyl-N-methyl-D-glucamino acetate, (III) wherein $R_4$ is $CH_2CO$, may be isolated by conventional methods, but is normally used in aqueous solution as prepared.

In a preferred embodiment of step (b) of the method of the present invention, said N,N-dialkylglycamine is reacted with said N-sulphoalkylating agent in a molar ratio sufficient to ensure substantially complete conversion of said glycamine to the corresponding hydroxypropane sulphonate. Typically molar ratios of from 1:1 to 1.5:1, preferably 1:1 to 1.05:1 (3 chloro-2-hydroxypropane sulphonic acid) are used. A temperature and a pH such that the hydroxyl group of the monosaccharide residue does not react are then maintained with stirring for from 1 to 30 hours, e.g. 20 hours, dependent upon temperature. Typically the temperature may be maintained between ambient and the temperature at which the degradation of the monosaccharide residue or the N-sulphoalkylating agent occurs e.g. up to 80° C., preferably up to 60° C., and the pH may for example be above pH 8.

Excess 3-chloro 2 hydroxy propane sulphonic acid, or its salts may be removed by hydrolysis using sodium hydroxide.

The product, N,N dialkylglycamino hydroxypropane sulphonate, e.g. N,N-dialkylglycamino-2-hydroxy-3-sulphopropane, (III), wherein $R_4$ is $CH_2CHOHCH_2SO_2$ may be isolated by conventional methods if required.

In step (c) of the method of the present invention, to produce the N,N-dialkylglycamine oxide, said N-N-dialkylglycamine, eg. N-dodecyl-N-methyl-D-glucamine is typically reacted with a suitable oxidising agent such that selective N-oxidation occurs, eg. stirring in the presence of an aqueous solution of hydrogen peroxide.

In the most preferred embodiment of step (c) of the method of the present invention, hydrogen peroxide is added to said N,N-dialkylglycamine in a ratio such that on completion of the oxidation reaction, an excess quantity of glycamine does not remain. For example a molar ratio of from 1:1 to 1.5:1 (by weight hydrogen peroxide: glycamine), eg. from 1:1 to 1.1:1 is acceptable although stochiometric amounts are usually preferred. Any excess glycamine would require further purification. Excess hydrogen peroxide can be removed using sodium sulphite.

The reaction is usually carried out in the presence of a small amount of transition metal ion chelating agent such as EDTA, at a temperature sufficient to maintain an adequate rate of oxidation whilst nevertheless avoiding the reaction of the hydroxyl group of the monosaccharide residue. Catalysts such as sodium bicarbonate and/or carbonate and/or carbon dioxide may be used to speed the reaction. Phosphonates such as acetodiphosphonates, amino tris (methylene phosphonate), ethylene diamine tetrakis (methylene phosphonates), diathylene triamine pentakis (methylene phosphonate) and higher members of the same series, and glycine bis (methylene phosphonate) are preferably present to further accelerate the reaction and to inhibit the formation of environmentally undesirable by products. Typical temperatures may be up to 100° C. e.g of from 40° C. to 90° C., such as 60° C., said temperature being maintained with, for from 2 to 6 hours, eg. 4 hours, dependent upon the temperature.

The product N,N-dialkylglycamine oxide, eg. N-dodecyl-N-methyl-D-glucamine N-oxide of structure (III) wherein $R_4$ is absent, may be isolated by conventional methods, but is normally used as prepared.

There is further provided N,N-dialkylglycamine derivatives made by a two stage synthesis whereby the starting compound (I), is subsequently reacted by methods (a) or (b) or (c) to produce a compound of formula (III).

Furthermore, the use of N,N-dialkylglycamine derivatives of formula (III) as surfactants is provided, including those made by the method of the present invention.

Typically said N,N-dialkylglycamine derivatives may be formulated in surfactant compositions which may additionally comprise, for example, other surfactants or synergists, antiperspirants, deodorants, lanolin or other skin softening or moisturising preparations, analgesics, antiseptics, emulsifiers, dispersants, soaps, polymeric thickening agents, wetting agents, foam controlling agents, perfumes and colouring.

The N,N-dialkylglycamine derivatives of the present invention have been shown to foam readily, being at the same time mild to the skin and eyes. Furthermore, they are biodegradable and in particular may be derived from renewable resources, e.g. a glucose derivative and a fatty alcohol.

The invention will be further illustrated by way of the following Examples:

EXAMPLE 1

Synthesis of N-lauryl-N-methyl-D-glucamine

Sodium lauryl sulphate 90% (w/w) (493.4 g, 1.67 m), N-methyl-D-glucamine (611.1 g, 3.15 m), and sodium hydroxide (60 g, 1.5 m) in 1055.7 g water were charged into a 5 liter autoclave vessel. After pressure testing with nitrogen at 200 psi the autoclave was then heated for 2 hours at 160° C. (maximum steam pressure generated was 88 psi). The reaction mixture was then cooled to give a white spongy material which was washed with water and methanol to remove impurities, and dried in a desiccator to give a white powder. Base value=96% pure.

| Charges: | Sodium lauryl sulphate 90% (w/w): | 493.4 g, 1.67 mole |
|---|---|---|
| | N-methyl-D-glucamine: | 611.1 g, 3.15 mole |
| | Water: | 1055.7 g |
| | Sodium hydroxide: | 60 g, 1.5 mole |
| Conditions: | Temperature: | 160° C. |
| | Time: | 2 hrs |

$$\begin{array}{c} CH_3NH \\ | \\ CH_2 \\ | \\ (CHOH)_4 \\ | \\ CH_2OH \end{array} + CH_3(CH_2)_nOSO_3Na \longrightarrow \begin{array}{c} CH_3N-(CH_2)_nCH_3 \\ | \\ CH_2 \\ | \\ (CHOH)_4 \\ | \\ CH_2OH \end{array}$$

n = 11, 13, 15, 17

Analysis: Base value: 149.4 mg KOH/g (97%)

FAB Mass spec: 336(M+H), 364(M+H), 392(M+H), 420 (M+H)

Melting point: 88°–90° C.

13C-NMR in $d_6$-DMSO: 14($CH_3$—$CH_2)_n$), 23–31($CH_2$ $_n$), 42 ($CH_3$—N), 60 (N—$CH_2$), 64($CH_2OH$), 70–72 (($CHOH)_4$).

1H-NMR in $d_6$—DMSO: 0.8(—$CH_3$,t,3H) 1.3 (—$CH_2$,s, 22H), 2.2 (—N—$CH_3$,d,3H), 3.4–3.7($CH_2$+CH,m,8H), 4.3–4.6 (OH,bm,5H)

EXAMPLE 2

Synthesis of N-lauryl-N-methyl-D-glucamino acetate

Sodium chloroacetate (20.7 g, 0.177 m) was dissolved in water (212 g) and N-lauryl-N-methyl-D-glucamine (64.5 g, 0.177 m) added stepwise in a small portions with stirring whilst the temperature of the reaction mixture was raised up to 60° C. After additions had been completed, the pH was adjusted to pH 9.0 with 0.5 g of 20% w/v sodium hydroxide. The reaction mixture was heated at 70° C. for 12 hours with the addition of a further 4.41 g of sodium chloroacetate being added at intervals in small portions. The product was obtained as a clear foaming solution.

| Charges: | Sodium chloroacetate | 25.11 g, 0.216 mole |
|---|---|---|
| | N-lauryl-N-methyl-D-glucamine | 64.5 g, 0.177 mole |
| | Water | 212 g |
| | 20% w/v sodium hydroxide | 1.4 g |

EXAMPLE 3

Synthesis of N-lauryl-N-methyl-D-glucamine-2-hydroxy-1-propane sulphonate

3-Chloro-2-hydroxy-1-propanesulphonic acid sodium salt (34.8 g, 0.177 m) was dissolved in water (212 g) and N-lauryl-N-methyl-D-glycamine added stepwise in small portions with stirring whilst the temperature of the reaction mixture was raised up to 60° C. After additions had been completed, the pH as adjusted to pH 9.0 with 1.5 g of 20% w/v sodium hydroxide. The reaction mixture was heated at 80° C. for 20 hours. The product was obtained as a clear foaming solution.

EXAMPLE 4

Synthesis of N-oxide of N-lauryl-N-methyl-D-glucamine

N-Lauryl-N-methyl-D-glucamine (393.63 g, 1.06 m) was suspended in water (1050 g) in a 2L jacketed vessel at 50° C. EDTA (1.7 g, 0.1% $^w$/w based on the total weight of the composition) suspended in warm water (30 g) was then added to the stirred suspension, followed by addition of sodium bicarbonate (17 g, 1% $^w$/w based on the total weight of the composition) dissolved in warm water (50 g). Hydrogen peroxide (34.75%) (104.35 g, 1.06 m) was then weighed out into a dropping funnel. Whilst the glucamine suspension was being stirred at 50° C., approximately 20 g of hydrogen peroxide was added in one batch. After 30 minutes the remaining hydrogen peroxide was added dropwise over a period of 30 minutes. After a further 20 minutes the milky suspension went clear and became less viscous. Total heating time 5 hours at 50° C. On cooling the final product turned into a white paste.

A 99% yield was obtained based on hydrogen peroxide assay.

We claim:
1. An N—$C_{10-20}$ alkyl-N-methylglycamine N-oxide.
2. A method of making N—$C_{10-20}$ alkyl-N-methylglycamine N-oxide, wherein said method comprises oxidizing an N—$C_{10-20}$ alkyl-N-methylglycamine to the N—$C_{10-20}$ alkyl-N-methylglycamine N-oxide.
3. A method of making N—$C_{10-20}$ alkyl-N-methylglycamine N-oxide, wherein said method comprises oxidizing an N—$C_{10-20}$ alkyl-N-methylglycamine to the N—$C_{10-20}$ alkyl-N-methylglycamine N-oxide with hydrogen peroxide as the oxidizing agent.

* * * * *